United States Patent [19]

Zimmer

[11] Patent Number: 4,776,342

[45] Date of Patent: Oct. 11, 1988

[54] ULTRASOUND IMAGING OF CALCULI

[75] Inventor: Hildebrand Zimmer, Ahrensburg, Fed. Rep. of Germany

[73] Assignee: U.S. Philips Corporation, New York, N.Y.

[21] Appl. No.: 916,063

[22] Filed: Oct. 6, 1986

[30] Foreign Application Priority Data

Oct. 10, 1985 [DE]  Fed. Rep. of Germany ....... 3536144

[51] Int. Cl.[4] ............................................. A61B 10/00
[52] U.S. Cl. ................................................ 128/660.01
[58] Field of Search ...................... 128/660, 328, 24 A, 128/804

[56] References Cited

U.S. PATENT DOCUMENTS 4,617,931  10/1986  Dory ...................................... 128/328
4,620,545  11/1986  Shene et al. ......................... 128/328
4,658,828   4/1987  Dory ...................................... 128/660

FOREIGN PATENT DOCUMENTS 3119295  12/1982  Fed. Rep. of Germany ...... 128/328

Primary Examiner—Francis J. Jawerski
Attorney, Agent, or Firm—Jack E. Haken

[57] ABSTRACT

During ultrasound checking of the results of lithotrity performed on biliary calculi, it is difficult to distinguish a calculus from crush. This problem is mitigated in accordance with the invention in that the ultrasound transducer (6) used for performing the ultrasound observation first receives a comparatively high electric power for a comparatively long period of time. As a result, the biliary calculus (4) or the crush is stirred up in the gallbladder (3); the size of the particles can be determined from the differences in behavior during settling in the gallbladder.

5 Claims, 1 Drawing Sheet

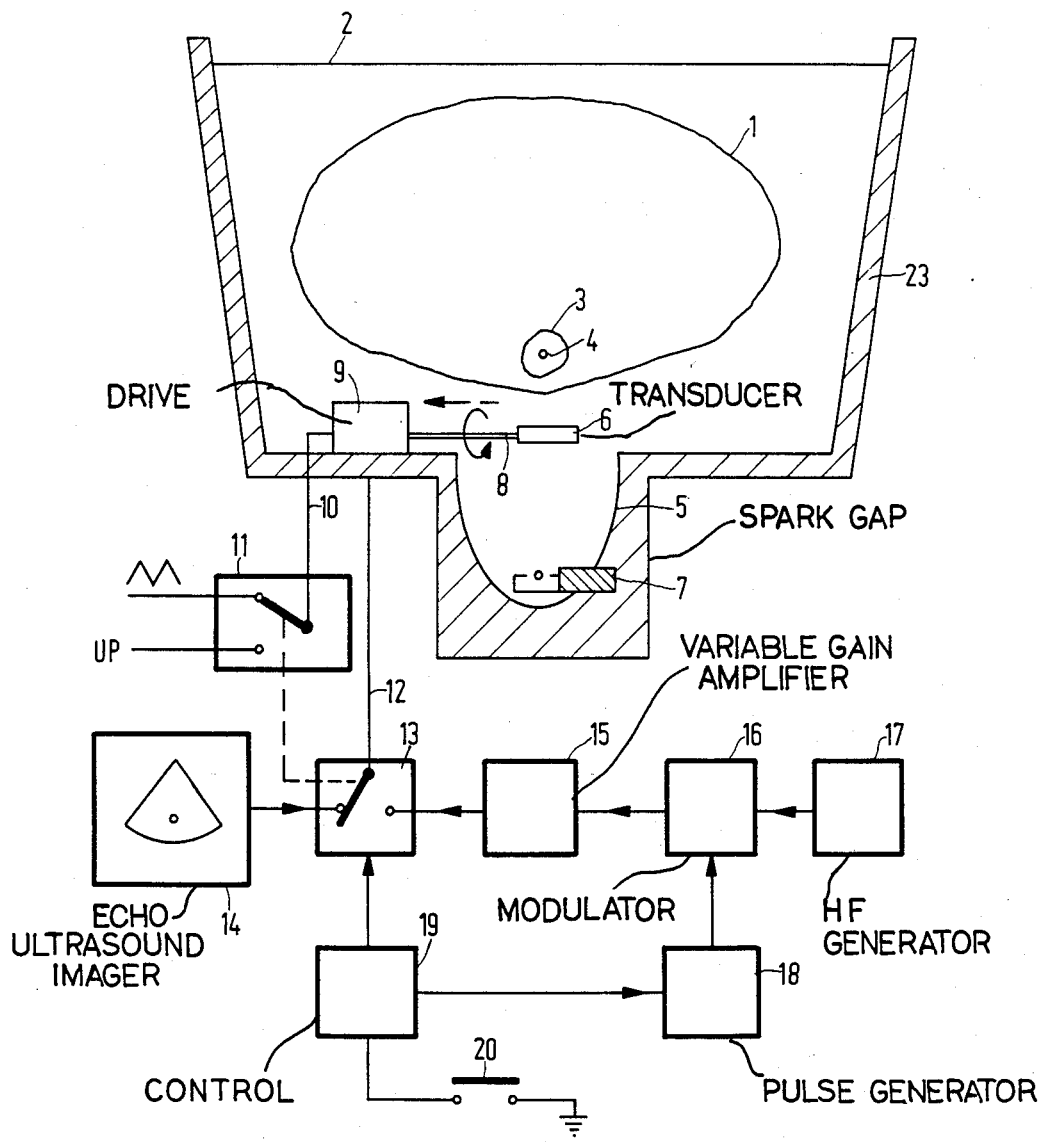

ULTRASOUND IMAGING OF CALCULI

The invention relates to an ultrasound examination method for use with lithotrity in bodies of living beings, where for ultrasound observation an ultrasound transducer periodically converts electric energy into acoustic energy during a transmission phase and converts acoustic echo signals into electric signals during a receiving phase. The invention also relates to an apparatus for performing such a method.

A device of this kind is known in principle from "Röntgenstrahlen", Vol. 49, 1983, pages 4 to 9. Therein, the crushing and the preceding localization of the calculus are performed with the aid of a device consisting of two X-ray sources and two image intensifiers; ultrasound localization is also mentioned therein, but it is stated that ultrasound cannot be used for checking the result of the treatment, because in the ultrasound image it is impossible to distinguish the crushed calculus from a non-crushed calculus. Even though these findings relate only to renal calculi, they hold good analogously for biliary calculi. In the ultrasound image a biliary calculus produces an echo which hardly deviates from the echo from crushed calculi on the fundus of the gallbladder.

It is an object of the present invention to provide a method of the kind set forth so that a compact biliary calculus can be distinguished from crushed biliary calculi in the gallbladder by means of ultrasound.

This object is achieved in accordance with the invention in that, prior to the ultrasound observation, an electric power which is high in comparison with the electric power applied during the transmission phase is applied to the ultrasound transducer during a period of time which is comparatively long in comparison with the transmission phase.

When a comparatively high electric power is applied to the ultrasound transducer during a comparatively long period of time, the transducer will produce a mechanical impulse because of the ultrasound radiation pressure, said impulse being sufficiently strong for stirring up the biliary calculus or the crushed calculi in the gallbladder. After stirring up, biliary calculi and crushed calculi can be clearly distinguished because, as a function of their size, they settle more or less quickly on the fundus of the gallbladder again because of their specific weight and the viscosity of the biliary liquid. During ultrasound observation of this process, the magnitude of the calculi or crushed calculi present in the gallbladder can be determined from the magnitude of the echoes from the targets as well as from the period of time required for settling. In order to enable stirring up of a biliary calculus, an acoustic power of at least 30 W (for a calculus weight of 1 g) should be applied for a period of between 5 ms and 250 ms.

In accordance with the invention, the ultrasound transducer has a triple function: Prior to the actual ultrasound examination, it stirs up the calculi or crushed calculi; during the ultrasound examination it supplies the transmission pulses and converts the acoustic echo signals into electric signals which serve to form an image of the stirred up crushed calculi.

The apparatus for performing the method, based on a liquid-filled tub for accommodating the body, a device for generating shock waves, a device for focussing the shock wave energy in one point in the tub, and an ultrasound transducer, is characterized in that it comprises a switching device which enables a high electric power to be applied to the ultrasound transducer in a first mode of operation for a comparatively long period of time, and to operate said transducer as a transmitter/receiver transducer of an ultrasound examination apparatus in a second mode of operation.

In a further embodiment in which the device for focussing the shock wave energy comprises an ellipsoid of revolution having two focal points, the shock wave being generated in one focal point and being focussed onto the other focal point, the ultrasound transducer is arranged on the connecting line between the two focal points. This embodiment is attractive in that the ultrasound energy enters the body from the same direction as the energy of the shock wave.

A further embodiment comprises a drive for displacing the ultrasound transducer perpendicularly to the connecting line between the focal points. If necessary, the ultrasound transducer can thus be prevented from masking a substantial part of the ellipsoid aperture, this damping the shock waves on their way to the focussing point.

In a further embodiment in accordance with the invention, the ultrasound transducer comprises a single transducer element. The ultrasound transducer could in principle also include a plurality (array) of ultrasound transducer elements which transmit and process the signals with a suitable, electronically controllable phase shift. In the present case, however, the biliary calculus or crush is situated at a defined distance from the ultrasound transducer, so that electronic focussing will not be necessary. Use can be made instead of fixed focussing, being determined by the construction of the ultrasound transducer element. It is relatively simple to design a single ultrasound transducer element so that it can generate the necessary acoustic intensities.

The invention will be described in detail hereinafter with reference to an embodiment shown in the accompanying drawing.

The drawing shows a cross-sectional view of a human body 1 which is arranged in a tub 23 filled with a liquid 2, for example water. The gallbladder is denoted by the reference numeral 3 and a calculus present therein by the reference numeral 4. In the centre of the bottom of the tub there is formed a recess 5 which is shaped as an ellipsoid of revolution and in one focal point of which there is arranged a spark gap 7 which is capable of generating shock waves which are focussed in the other focal point of the ellipsoid of revolution. Between the two focal points, that is to say on the symmetry axis of the ellipsoid of revolution, there is arranged an ultrasound transducer element 6 having a resonant frequency of, for example 3 MHz. It is focussed onto the focal point in which the shock waves generated by the spark gap 7 converge. During formation of the shock waves, or the ultrasound examination, the biliary calculus 4 or the deepest point of the gallbladder 3 will be situated in this focal point.

The ultrasound transducer 6 is connected to a shaft 8 which extends horizontally, that is to say perpendicularly to the connecting line between the focal points. A drive 9 acts on this shaft; the drive receives, via a lead 10 and a switching device 11, either a delta control signal or a constant voltage UP (possibly ground potential). When the delta control signal is applied to the drive device 9, the ultrasound transducer will perform a reciprocating angular movement with a period of, for example 100 ms, said movement covering a given sector which extends perpendicularly to the plane of drawing and through the second focal point of the ellipsoid 5, so that ultrasound can be transmitted or received in this direction.

Via a line 12, the ultrasound transducer 6 is connected to a further switch 13, one side of which is connected to the components of a conventional ultrasound examination device 14 (transmitter, receiver, scan converter, monitor) for real time sector image display its other side being connected to the output of a variable gain power amplifier 15. Via a modulator 16, the input of the amplifier 15 is connected to a high-frequency generator 17. The high-frequency generator 17 supplies a voltage having a frequency of 3 MHz, i.e. the resonant frequency of the ultrasound transducer 6. The modulator 16 is controlled by a pulse generator 18 which supplies pulses having a duration which is adjustable between 5 ms and 250 ms. The pulse duration should not be too long or too short. In the case of very short pulses a very high power will be required, whilst in the case of very long, comparatively low-power pulses the biliary calculi will only start to float instead of being stirred up. It is only when such a pulse is supplied that the modulator 16 will supply an output signal having the frequency of the oscillation generated by the generator 17; when the pulse generator does not supply a pulse, the output signal of the modulator 16 will be zero. When a switch 20 is actuated by the operator, a control device 19 will switch the switching devices 11, 13 briefly from the position shown to the position which is not shown, thus activating the pulse generator 18, for example a monostable multivibrator, so that the latter will generate a single pulse.

The device operates as follows. Prior to the generating of the shock wave, an ultrasound examination is performed during which the biliary calculus is localized. The body 1 is then positioned in the tub 23, using a lifting device (not shown), so that the biliary calculus 4 on the fundus of the gallbladder is situated at the location of the second focal point; this can be recognized in the ultrasound image in that the image of the biliary calculus is situated in a given position on the display screen of the display device of the examination device 14. During the ultrasound examination the switching devices 11 and 13 are in the position shown in the drawing. The delta signal is subsequently applied to the motor drive 9 so that it will perform a periodic reciprocating angular motion, during each period of approximately 100 ms the ultrasound transducer 6 being briefly actuated (for example, during 1 $\mu$s) with a constant pulse repetition frequency of 256 times in the transmission phase, whilst during the period of time elapsing between two transmission pulses the ultrasound echoes are converted into electric signals which are digitally stored in the scan converter and converted into an ultrasound sector image displayed on the monitor.

When the biliary calculus and the ultrasound observation have thus progressed to the second focal point of the ellipsoid of revolution, the spark gap is fired one or more times. The crush possibly formed settles on the fundus of the gallbladder 3, i.e. at the same location where previously the compact biliary calculus was present.

In order to enable checking of the crushing of the calculus, the switch 20 is activated, so that on the one hand the circuit 18 for generating pulses is activated and on the other hand the switching devices 11, 13 are set to the position not shown for a period of time which terminates briefly after the end of the pulse. In this position of the switching device 11 the ultrasound transducer occupies a defined angular position in space, that is to say the position in which an ultrasound beam generated thereby passes through the biliary calculus 4. The electric power applied to the ultrasound transducer 6 in this position of the switching device 13 is so high that the acoustic energy generated by the transducer suffices to lift a biliary calculus in the gallbladder a few centimetres. Depending on the weight of the biliary calculus, being substantially reduced by the upward force exerted by the biliary liquid, the lift will be larger or smaller; in the case of a weight of 50 mg (corresponding to a biliary calculus of 1 cm$^3$) the energy amounts to approximately 200 Ws (for a lift of 5 cm). As a result the biliary calculus or the crush is stirred up in the gallbladder and settling can be observed and evaluated during the ultrasound examination phase which directly succeeds stirring up.

The aperture of the ellipsoid of revolution is substantially larger than the diameter of the ultrasound transducer element. As a result, it masks the biliary calculus only insignificantly from the shock wave emitted by the spark gap 7; that is to say, in any case when it is not situated too near to the second focal point. In order to preclude any masking or even damaging of the ultrasound transducer by the shock wave, it may be useful to displace the transducer 6, using a drive (not shown) so far in the lateral direction, prior to the ignition of the spark gap 7, that it no longer covers the aperture of the ellipsoid of revolution.

The present device utilizes a tub 23 in which the body 1, a coupling liquid 2 (water) etc. are situatd. It is alternatively possible, however, to enclose the coupling liquid in a flexible bag or tube and to couple the spark gap to the body via the bag or tube. The ultrasound transducer must then be accommodated in the tube or the bag.

What is claimed is:

1. A method for imaging calculi within a region of a body comprising the steps of:
   first directing first pulses of sonic energy into the region, said first pulses having a length and power level which is sufficient to stir up any calculi within the region but not to crush said calculi; and then
   directing second pulses of ultrasonic energy into the region and forming images of the stirred up calculi from echoes of said second pulses.

2. The method of claim 1 wherein said region of the body is the gall bladder.

3. The method of claim 2 wherein a single ultrasound transducer is used to produce both the first and second pulses in the region.

4. The method of claim 2 wherein the step of first directing pulses of sonic energy into the region comprises applying relatively long, relatively high power electrical pulses to a transducer to generate a shock wave in the region.

5. The method of claim 2 further comprising the step of examining the echo ultrasound images as the stirred up calculi settle to differentiate between solid calculi and calculus fragments.

* * * * *